(12) United States Patent
Wowk

(10) Patent No.: US 6,391,224 B1
(45) Date of Patent: May 21, 2002

(54) POLYVINYL ALCOHOL COMPOUNDS FOR INHIBITION OF ICE GROWTH

(75) Inventor: Brian Wowk, Corona, CA (US)

(73) Assignee: 21st Century Medicine, Inc., Rancho Cucamonga, CA (US)

( * ) Notice: Subject to any disclaimer, the term of this patent is extended or adjusted under 35 U.S.C. 154(b) by 0 days.

(21) Appl. No.: 09/400,791

(22) Filed: Sep. 21, 1999

Related U.S. Application Data

(60) Provisional application No. 60/143,587, filed on Jul. 13, 1999, provisional application No. 60/128,142, filed on Apr. 7, 1999, provisional application No. 60/127,158, filed on Mar. 31, 1999, and provisional application No. 60/101,194, filed on Sep. 21, 1998.

(51) Int. Cl.$^7$ .................................................. C09K 3/18
(52) U.S. Cl. ................................ 252/70; 47/2; 106/13; 252/71; 252/73; 252/77
(58) Field of Search .............................. 252/70, 71, 73; 106/13; 239/2.1; 47/2

(56) References Cited

U.S. PATENT DOCUMENTS

| | | | |
|---|---|---|---|
| 3,045,394 A | | 7/1962 | Coulter et al. .................. 427/4 |
| 3,399,991 A | * | 9/1968 | Littler .......................... 504/330 |
| 3,802,624 A | | 4/1974 | Kühne et al. ................. 239/2.1 |
| 4,484,409 A | | 11/1984 | Caple et al. ...................... 47/2 |

FOREIGN PATENT DOCUMENTS

| | | | |
|---|---|---|---|
| FR | 2607821 | * | 6/1988 |
| JP | 58-70828 | * | 4/1983 |
| JP | 59-122573 | * | 7/1984 |
| JP | 9-31448 | * | 2/1997 |
| WO | WO 91/10361 | | 7/1991 |
| WO | WO 96/30459 | | 10/1996 |
| WO | WO 97/16062 | | 5/1997 |
| WO | WO 97/38950 | | 10/1997 |

OTHER PUBLICATIONS

Arthur L. DeVries et al., Freezing Resistance in Some Antarctic Fishes, *Science*, vol. 163, Mar. 7, 1969, pp. 1073–1075.
Irving M. Klotz, *Polyhedral Clathrate Hydrates*, pp. 5–26. (no date).
Gerald Caple et al., Polymeric Inhibition of Ice Nuclei Active Sites, *Cryo–Letters*, vol. 4, 1983, pp. 51–58. (no month).
G. M. Fahy et al., Vitrification as an Approach to Cryopreservation, *Cryobiology*, vol. 21, 1984, pp. 407–426. (no month).
Gregory M. Fahy et al., Physical Problems with the Vitrification of Large Biological Systems, *Cryobiology*, vol. 27, 1990, pp. 492–510. (no month).
Robin L. Sutton et al., Devitrification in Butane–2,3–Diol Solutions Containing Anti–Freeze Peptide, *Cryo–Letters*, vol. 14, 1993, pp. 13–20. (no month).
S. Naitana et al., Polyvinyl alcohol as a defined substitute for serum in vitrification and warming solutions to cryopreserve ovine embryos at different stages of development, *Animal Reproduction Science*, vol. 48, 1997, pp. 247–256. (no month).
V. Sommerfeld et al., Cryopreservation of Bovine in Vitro Produced Embryos Using Ethylene Glycol in Controlled Freezing or Vitrification, *Cryobiology*, vol. 38, 1999, pp. 95–195. (no month).
XP–002131673, Zh Nagano–Ken Nokyo Chiiki Kaihatsu Kiko, Database WPI, Derwent Publications Ltd., London, GB, Dec. 14, 1993, 2 pages.
XP–002131762, S. Naitana et al., Polyvinyl alcohol as a defined substitute for serum in vitrification and warming solutions to cryopreserve ovine embryos at different stages of development, *Chemical Abstracts*, vol. 128, No. 12, Mar. 23, 1998, p. 1.
XP–002131763, Ladislau Csomontany et al., Deicing mixture, *Chemical Abstracts*, vol. 79, No. 26, Dec. 31, 1973, p. 1.
Derwent Abstract No. 1983–21298K, abstract of Japanese Patent Specification No. 58–011578 (Jan. 1983).*
Derwent Abstract No. 1990–091474, abstract of Chinese Patent Specification No. 1032352 (Apr. 1989).*
Derwent Abstract No. 1994–021834, abstract of Japanese Patent Specification No. 53–28859 (Dec. 1993).*
Derwent Abstract No. 1994–032868, abstract of Soviet Union Patent Specification No. 1785672 (Jan. 1992).*

* cited by examiner

*Primary Examiner*—Anthony Green
(74) *Attorney, Agent, or Firm*—Jay P. Hendrickson

(57) ABSTRACT

Polyvinyl alcohol and related compounds are provided that inhibit the freezing of water and water solutions. These synthetic compounds preferentially bind and inhibit ice nucleating surfaces in a manner similar to natural antifreeze proteins. The resulting inhibition allows water and water solutions to supercool without ice formation to temperatures below the thermodynamic freezing point. The freezing inhibition occurs at concentrations as small as one part per million, although concentrations up to one part per hundred are preferred. These polyvinyl alcohol additives are very useful for enhancing the performance of antifreeze formulations, biological cryopreservation solutions, and for preventing frost damage to plants and other industrial products and processes.

34 Claims, No Drawings

POLYVINYL ALCOHOL COMPOUNDS FOR INHIBITION OF ICE GROWTH

This application claims the benefit of priority under 35 U.S.C. § 119(e) from the following Provisional Application Nos.: 60/101,194, 60/127,158, 60/128,142 and 60/143,587, filed Sep. 21, 1998, Mar. 31, 1999, Apr. 7, 1999 and Jul. 13, 1999, respectively.

FIELD OF THE INVENTION

The invention relates generally to the field of inhibition of ice growth. More specifically, the invention relates to a method for inhibition of ice growth using polyvinyl alcohol and related compounds.

BACKGROUND OF THE INVENTION

Preventing the freezing of water, and solutions that contain water, is a problem of substantial environmental, agricultural, industrial, and biomedical interest. Ice on walkways, roads and aircraft wings constitute an environmental hazard to transportation. Ice formation on and inside plants causes expensive damage to crops and gardens. Freezing of antifreeze solutions, pipeline contents, paints, wet concrete and other aqueous solutions subjected to cold temperatures are issues of concern for industry. Avoiding ice formation during cold storage of tissue is also an important problem in cryobiology.

Below a critical temperature (the equilibrium freezing point), the crystallization of water into ice becomes thermodynamically favored. The freezing point of water can be lowered by adding solutes that interact with water, thereby interfering with the ability of water molecules to organize into ice crystals. The resulting freezing point depression is termed "colligative" freezing point depression. Colligative freezing point depression is the physical basis on which essentially all currently used antifreeze agents (such as glycols and salts) operate. The disadvantage of colligative freezing point depression is that large quantities of solutes (10% or more) are required to lower the freezing point by even a few degrees Celsius.

Beyond colligative freezing point depression, there is another approach that can be used to prevent ice formation and growth. At temperatures above −40° C. water cannot freeze unless the freezing is catalyzed by ice that has already formed, or by impurities called ice nucleating agents (INAs). It is therefore possible for water and water solutions to exist as "supercooled" liquids at temperatures significantly below the freezing point. In practice, significant supercooling is rarely observed in nature (with the exception of microscopic water droplets in rain clouds). This is because INAs are ubiquitous in the environment, causing water to almost invariably freeze if it is cooled slightly below the freezing point. Even highly purified laboratory grade water contains significant background concentrations of INAs. If INAs can be removed or inhibited, water and water solutions can be supercooled to temperatures many degrees below the freezing point without actually freezing.

Cold-hardy plants, insects, and fish have evolved antifreeze proteins that selectively adsorb onto the surface of ice or INAs, thereby preventing water molecules from coming into contact with surfaces that trigger ice growth (Devries, A. L., and Wohlschlag, D. E. "Freezing resistance in some Antarctic fishes" Science 163, pp. 1074–1075, 1969). Antifreeze proteins thus act as non-colligative antifreeze agents, and very small concentrations (less than 1%) are able to suppress the temperature at which ice forms by several degrees. Soon after the original discovery of antifreeze proteins, it was speculated that "many polymeric molecules (not just proteins) ought to be able to inhibit nucleation (of ice) in this way" (Klotz, I. M. in "The Frozen Cell" pp. 5–26. J. & A. Churchill, London, 1970). These speculations opened the door to the possibility that inexpensive synthetic compounds might be found with non-colligative antifreeze activity.

SUMMARY OF THE INVENTION

The present invention provides compounds that adsorb onto ice and especially ice nucleating agents, thereby inhibiting said agents, and thereby permitting supercooling of water and water solutions to temperatures below the freezing point without actually freezing.

The invention further provides additives that in small concentrations prevent water from freezing at temperatures below 0° C. Such additives are useful in industry and agriculture to prevent irrigation water from freezing in pipes or on plants subjected to cold weather. Such additives may also be useful in preventing water inside plants from freezing when irrigation water or soil contain the additives. Such additives may also be further useful in preventing water from freezing on surfaces such as roads or aircraft wings in cold weather.

Still further, the invention provides additives that in small concentrations prevent solutions of water from freezing at temperatures below the solution freezing point. Such additives will augment the performance of antifreeze solutions used as engine coolants and deicing solutions by permitting said solutions to endure temperatures below their rated freezing point without freezing. Such additives also augment the cold tolerance of paints, cements, concretes, and other aqueous media that are stored or cured under conditions that entail a risk of freezing.

The additives of the present invention reduce or inhibit the formation of ice in biological materials undergoing cryopreservation. Such additives are of particular utility for cryopreservation by vitrification, a cryopreservation method which requires complete suppression of ice formation.

The additives of the present invention can facilitate hypothermic preservation of biological materials in a supercooled state below 0° C. These additives reduce the likelihood of freezing occurring in the supercooled state and/or make lower preservation temperatures possible.

The invention additionally provides compounds that are able to substitute for biologically-derived antifreeze proteins in diverse applications, as well as compounds that inhibit growth or recrystallization of ice. Compounds that adsorb onto ice nucleating agents for purposes of extracting ice nucleating agents from water and water solutions are also provided. The compounds of the present invention can also be dispersed in the atmosphere to alter precipitation in rain clouds by inhibiting atmospheric ice nucleating agents.

These and other aspects of the present invention will be apparent to those of ordinary skill in the art in light of the description below and appended claims.

DESCRIPTION OF THE PREFERRED EMBODIMENTS

The present invention provides methods for preventing the freezing of water and solutions that contain water using inexpensive compounds with non-colligative antifreeze activity.

Polyvinyl alcohol (PVA) is a water-soluble polymer consisting of an alkane backbone with hydroxyl groups attached at every second carbon. It thus consists of repeating CH2CHOH units. It is an inexpensive high tonnage industrial chemical used in adhesives, textile manufacturing, food packaging, cosmetics, and pharmaceutical preparations. It is non-toxic, environmentally friendly, and biodegradable.

It has been discovered in this invention that PVA and related compounds act as non-colligative antifreeze compounds that preferentially adsorbs onto ice nucleating particles and surfaces in a manner similar to natural antifreeze proteins. As the examples below show, very small concentrations of PVA (as little as 1 part per million) significantly enhance the ability of water and water solutions to supercool without ice formation.

However, we find that PVA is very effective as an ice inhibiting agent at concentrations ranging from 100 parts per billion to tens of percent. Concentrations ranging from 0.01% to 10% w/w are preferred. Concentrations ranging from 0.1% to 2% w/w are more preferred. Concentrations ranging from 0.3% to 1% w/w are most preferred. It will be understood by those skilled in the art that the choice of PVA concentration in any antifreeze application will also depend on factors other than maximum ice inhibition, including cost and solution viscosity considerations.

PVA is commercially available in molecular weights ranging from approximately 5 kDa (kilo daltons) to hundreds of kDa. Lower molecular weights are preferred because smaller polymer molecules are more mobile in solution. Greater mobility results is lesser viscosity increase when PVA is added to solutions, and greater ability of the PVA molecules to rapidly diffuse through the solution and encounter ice nucleating agents (INAs) so that they may be inactivated. In particular, PVA of molecular weight less than 30 kDa, and even more preferable, PVA of molecular weight less than 10 kDa. PVA of molecular weight 150 kDa was found to be somewhat effective as an ice inhibiting agent, but much less effective at 1% concentration than PVA of molecular weight of 30 kDa or less.

PVA of molecular weight 1 kDa was custom-synthesized and found to have very favorable ice inhibition and viscosity properties. This molecule consists of a mean number of 20 vinyl alcohol monomer units. Even smaller molecules are contemplated. For reasons disclosed below, as few as 3 to 5 contiguous vinyl alcohol units can be sufficient for binding to ice nucleating surfaces. Thus, PVA oligomers such as 1,3,5,7 heptanetetrol and homologues or derivatives, are also believed to be active as ice inhibiting compounds. Such small molecules may have special utility in biological applications, for which they will more easily pass through endothelial tight junctions, or perhaps even cell membranes.

The advantages of low molecular weight PVA do not preclude the use of higher molecular weight PVA in ice inhibiting applications. It is possible to contemplate antifreeze applications in which the properties of high molecular weight PVA are used to advantage. For instance, in addition to inhibiting ice nucleation events, high molecular weight PVA might be used to impede ice growth that is already in progress by imparting high viscosity to the solution.

PVA is typically manufactured by polymerization of vinyl acetate and subsequent hydrolysis of polyvinyl acetate. PVA is commercially available as partially hydrolyzed (some residual vinyl acetate units) or fully hydrolyzed (no residual vinyl acetate) polymer. Fully hydrolyzed PVA tends to self-associate in solution, forming turbid solutions or even gels if left standing. This problem is particularly severe at high molecular weights, although even low molecular weight fully-hydrolyzed PVA can form turbid solutions in the presence of other solutes. Self-association limits the availability of PVA molecules to bind with ice nucleating surfaces. Fully hydrolyzed PVA is therefore not preferred for this invention.

The efficacy of PVA for inhibiting ice formation in concentrated cryoprotectant solutions was studied as a function of mole percent hydrolysis of the parent polyvinyl acetate polymer. Efficacy was found to be greatest for PVA of between 80% and 97% hydrolysis. Efficacy dropped dramatically as the percent hydrolysis was reduced below 80%. PVA that is 80% hydrolyzed has a mean number of four vinyl alcohol units for every vinyl acetate unit in the copolymer. These results therefore suggest that four (or perhaps 3 or 5) contiguous vinyl alcohol units are required for effective adsorption onto ice nucleating surfaces. It is thus apparent that molecules other than pure PVA or PVA copolymers can be similarly effective for this invention. In particular, any molecules containing 1,3,5,7 hydroxy, or 1,3,5,7,9 hydroxy patterns as part of the molecule are also expected to selectively bind to ice nucleating particles and surfaces.

Partially hydrolyzed PVA (i.e. polyvinyl alcohol/vinyl acetate copolymer) is advantageous for reducing PVA self-interaction in solution, thereby reducing viscosity and turbidity, and maximizing molecular mobility. To this end, it is advantageous to incorporate the most vinyl acetate to the copolymer that may be incorporated without impacting ice inhibition effectiveness. Copolymers with 10 to 20 mole percent vinyl acetate content (corresponding to 80%–90% hydrolysis) are therefore preferred for this invention.

It will be understood by those skilled in the art that other modifications to the PVA polymer are possible that will also reduce self-interaction in solution. In particular, hydroxyl groups can be replaced with alkoxyl groups. More specifically, some or all of the hydroxyl groups in PVA may be replaced by methoxyl groups. Compared to acetate groups, methoxyl groups have the advantage that the hydrogen bonding ability of the oxygen atom is preserved. It's therefore possible that more than 20% of the hydroxyl groups can be replaced by methoxyl groups without impacting ice inhibition effectiveness.

PVA produced by hydrolysis of polyvinyl acetate has atactic stereochemistry (the hydroxyl groups occur randomly on the left and right sides of the Fischer projection of the polymer). As an alternative to atactic PVA, stereoregular PVA can also be produced. In particular, synthesis routes are available for isotactic PVA (e.g. hydrolysis of polyvinyl tert-butyl ether) and preferentially syndiotactic PVA (e.g. hydrolysis of polyvinyl pivalate). It was discovered during development of this invention that isotactic PVA is ineffective as an ice inhibiting agent. This suggests that syndio diads are involved in the binding mechanism of PVA onto ice nucleating surfaces. Atactic and syndiotactic PVA are therefore the preferred stereochemical forms of PVA for this invention.

It has been noted elsewhere that the addition of appendages and complexes onto antifreeze protein molecules can enhance their activity, possibly by increasing the area of an ice nucleating surface that is effectively blocked by a bound protein (Wu, D. W., Duman, J. G., and Xu, L. "Enhancement of insect antifreeze protein activity by antibodies" *Biochim Biophys Acta* 1076, pp. 416–420, 1991). It is therefore anticipated that the ice blocking activity of PVA compounds can also be further enhanced by adding molecular appendages that increase the lateral extent of the molecule when it is bound to an ice nucleating surface. A portion of the hydroxyl groups in PVA (preferably not exceeding 20% of the total number of hydroxyls) can be easily converted into ester or ether linkages for connecting these appendages.

A diverse variety of further modifications to PVA polymers and oligomers that would not interfere with ice inhibiting properties can be contemplated. In particular, since the binding mechanism to ice nucleating surfaces is a polar interaction, any molecule containing a carbon chain with polar groups (especially hydroxyls) located with the same spacing as PVA (every other carbon) would also be expected to inhibit ice. Within this paradigm there is broad latitude to replace non-hydroxyl hydrogens in PVA with other moeties, provided the moeties are not so large that they sterically hinder the hydroxyls.

Examples 1–3 demonstrate the effectiveness of a PVA compound for promoting supercooling of water. The effectiveness of PVA for inhibiting ice formation in supercooled water will in general depend on the density of INAs, the concentration of PVA, and the volume of water. A mass ratio of at least 100,000 parts PVA per one part INA is preferred. Larger water volumes are expected to supercool less because opportunities for random ice nucleation events are greater.

Examples 3 and 8 demonstrate the effectiveness of a PVA compound at inhibiting ice nucleation caused by a bacterial INA. This demonstration is significant because ice nucleating proteins of bacterial origin are believed to be a major source of background INAs in the environment. In particular, ice nucleating bacteria such as *Pseudomonas syringae* and *Erwinia herbicola* present on plant surfaces are believed to be the primary cause of plant frost damage at temperatures between −6° C. and 0° C.

Various prior art methods have been proposed to control ice nucleating bacteria on plants at risk of frost damage. These methods include applying bactericide (U.S. Pat. Nos. 4,834,899 and 5,079,868), bacteriophages (U.S. Pat. No. 4,375,734) and displacing INA bacteria with similar bacteria that don't produce INA proteins (U.S. Pat. Nos. 4,045,910/ 4,161,084/ 4,432,160). The methods most similar to the present invention are proposals to spray solutions containing natural (U.S. Pat. No. 4,601,842) or synthetic (U.S. Pat. No. 4,484,409) ice nucleation inhibiting compounds onto plants. The present invention is superior to these inventions because PVA compounds are much less expensive than natural antifreeze proteins, and because PVA compounds are known to be biodegradable and non-toxic (FDA-approved as an indirect food additive), unlike the polymers of U.S. Pat. No. 4,484,409.

Many possible embodiments of the present invention for protecting plants against freezing damage will be apparent to those skilled in the art. In one embodiment, PVA compounds can be included in water sprays that are used to spray the surface of plants at acute risk of freezing. In another embodiment, PVA compounds can be included in normal irrigation water on a long-term basis. Only very small concentrations would be necessary because evaporation would concentrate the compound on plant surfaces. In another embodiment, low molecular weight PVA compounds might be included in irrigation water, fertilizer formulations, or plant potting soil so that these compounds are absorbed by plants to provide freezing protection inside plant tissues. In another embodiment, PVA compounds might be dispersed in the form of a powder on plants. In still another embodiment, PVA can be included as a component of other antifreeze solutions used for plant frost protection. For example, PVA of suitable molecular weight might be used instead of other polymers as the thickening agent of the invention in U.S. Pat. No. 5,653,054.

Solutions containing PVA compounds are expected to exhibit a cleansing action against INAs, adhering to INAs so that INAs will be washed off surfaces, eventually depleting the surfaces of INA material. It has even been suggested that INA binding agents might exhibit a specific bactericidal activity against INA bacteria by blocking bacterial cell wall transport channels (U.S. Pat. No. 4,484,409).

In addition to inhibition of plant freezing, it is also anticipated that PVA compounds might inhibit freezing of animal or human peripheral tissue that is subjected to cold temperatures. When exposed to sub-freezing temperatures, skin will typically supercool by several degrees until ice suddenly forms, causing the characteristic sting and injury of frostbite. PVA compounds applied to the skin in skin care products would be expected to inhibit ice nucleation events, allowing skin to cool to lower temperatures before actually freezing. The most effective formulations might also include other non-toxic cryoprotectants, such as glycerol and/or propylene glycol to augment PVA's non-colligative protection with colligative lowering of the freezing point. In another embodiment, the PVA compounds might simply be included in cleansing products for the purpose of removing INA material from skin before cold exposure.

In non-biological applications, it is anticipated that the present invention is broadly useful for preventing the freezing of water at temperatures a few degrees below freezing. PVA compounds may have utility as non-colligative antifreeze agents in a variety of industrial settings where it is desirable to inhibit the freezing of water, and permissible to add small quantities of solute. PVA compounds may be especially useful for inhibiting freezing of water which is present in small quantities as a contaminant in hydrophobic fluids, such as fuels. In this embodiment, the PVA compound would be formulated with a hydrophobic group rendering the molecule soluble in the hydrophobic fluid, but still capable of partitioning into the water phase to inhibit ice formation.

Examples 4 and 9 document the effectiveness of a PVA compound for enhancing supercooling in solutions that contain significant quantities of other solutes. In general, greater supercooling is possible in the presence of solutes than is possible in pure water. The supercooling enhancement achievable with PVA compounds is also greater in water containing solutes than in pure water.

The most obvious instance of solutions in which supercooling promotion would be beneficial is antifreeze solutions. Antifreeze solutions are typically rated to provide freezing protection down to a temperature equal to the freezing point of the solution. However this generally understates the protective potential of antifreeze solutions because significant supercooling of the solutions can and does occur. The addition of PVA compounds to conventional antifreeze solutions would allow supercooling to occur more reliably and to deeper temperatures than ordinarily occurs. This would provide a greater margin of safety in freeze protection. This would benefit antifreeze solutions (such as engine coolant antifreeze) and deicing solutions (keeping surfaces ice free longer after deicing).

Other uses for facilitating supercooling of aqueous solutions can also be contemplated. Any water-based product that can be harmed by freezing during either storage or use will benefit from the addition of non-colligative antifreeze compounds. For example, products that may be exposed to cold during a curing process will benefit from the additives of this invention. More specifically, water-based paints can be protected against freezing during either storage or drying by small amounts of PVA. Setting cement and concrete can also be protected against freezing by these additives.

Cryopreservation of biological material by vitrification is an extreme example of supercooling. Large concentrations of colligative solutes (cryoprotectants) are used to make preservation solutions with freezing points below −20° C. By cooling rapidly it is then possible to supercool these vitrification solutions to below −120° C. with no ice formation. At temperatures below −120° C. the supercooled solution undergoes a transition to a glassy solid, and is said to be "vitrified".

The supercooling ability of vitrification solutions is sensitively dependent upon cryoprotectant concentration. A critical cryoprotectant concentration, denoted Cvit, is necessary to successfully supercool without ice formation at a given cooling rate. The toxicity of vitrification solutions is also sensitively dependent upon concentration, often rising non-linearly as Cvit is approached. Means to reduce Cvit by even a few percent are therefore extremely valuable. Example 5 demonstrates that even very small concentrations of a PVA compound can significantly reduce Cvit for vitrification solutions (up to 5% when the cryoprotectant is glycerol).

Vitrification solutions tend to be unstable with respect to ice formation during rewarming following cooling. Vitrified solutions often freeze extensively during rewarming (a process termed "devitrification") unless rewarming is very rapid. This ice formation occurs because ice nucleation often occurs invisibly and extensively during the cooling process. The nucleated ice then becomes evident as rewarming carries the solution trough the temperature range in which ice grows rapidly. Ice formation during rewarming could be prevented if the original nucleation events could be suppressed. The present invention provides for this. Example 6 shows dramatic inhibition of "devitrification" by a PVA compound. This aspect of the invention is very valuable because it relaxes the stringent rewarming rate requirements for vitrification, reducing or removing the need for expensive radio frequency heating systems that are otherwise required for rapid warming of large samples.

While PVA is an excellent ice nucleation inhibitor, it is a poor colligative cryoprotectant. There is therefore a balance to be achieved in vitrification applications between the non-colligative antifreeze benefit of PVA, and the colligative antifreeze benefit of other cryoprotectants. In particular, if replacement of conventional cryoprotectant by PVA in a vitrification solution is contemplated, then the optimum PVA concentration will be between 0.5% and 2%, depending on the cryoprotectant being replaced. At lower concentrations, the nucleation inhibiting potential of PVA will not be fully exploited. At higher replacement concentrations, the loss of colligative activity in the solution outweighs the gain in ice nucleation suppression. In particular, if large concentrations of colligative cryoprotectant are replaced by PVA, very few ice growth sites will form, but they will grow to a large size.

Example 7 shows inhibition of ice during cooling of a vitrification solution using only 1 part per million concentration of a PVA compound. Observations of this nature are compelling evidence that PVA inhibits ice formation by direct interaction with ice nucleating surfaces, not by altering physical properties of the solution, such as viscosity or surface tension.

The preservation of tissues and organs at hypothermic temperatures (temperatures near 0° C.) for several hours or days is also an active area of interest in cryobiology. One approach to hypothermic preservation involves maintaining organs in a supercooled state at temperatures slightly below the freezing point (Conn Med 59, pp. 387–99, 1995). Supercooled states are inherently at risk of freezing. The inclusion of ice nucleation inhibiting compounds of the present invention in supercooling preservation solutions reduces this risk, expanding the frontiers of this field.

Example 10 shows that a PVA compound can inhibit ice formation even more effectively than a powerful antifreeze protein. The compounds of this invention are also able to substitute for antifreeze proteins in diverse applications wherein the role of the antifreeze protein is to control ice. (In some applications, antifreeze proteins convey cold protection to biological systems by ion channel blocking or other mechanisms not related to ice inhibition.) For example, PVA compounds might be used instead of antifreeze proteins for inhibition of ice recrystallization. It is especially advantageous to replace antifreeze proteins with the compounds of this invention because PVA compounds can be produced thousands of times less expensively than antifreeze proteins.

The binding affinity of the compounds of this invention for INAs makes it possible to contemplate systems designed to cleanse solutions of INAs instead of merely inhibiting them. In one embodiment, water or other aqueous solutions could be passed through columns (repeatedly, if necessary) containing high molecular weight and/or cross linked PVA that is water insoluble. In another embodiment, the column material might contain a PVA compound as a covalent appendage on an insoluble resin or other substrate. It is anticipated that such columns would remove INAs from fluids passed through them by adsorption onto the PVA. In still another INA cleansing embodiment, a PVA compound would be introduced into the solution and then removed by exposure to material with a binding affinity for an appendage on the PVA molecule, or PVA itself INA cleansing processes would be particularly useful for vitrification solutions, or solutions used for supercooled hypothermic preservation.

Environmental INAs play a pivotal role in initiating precipitation in the atmosphere. Inexpensive INA inhibitors such as PVA compounds may therefore also have utility for weather modification, as discussed in U.S. Pat. No. 4,484,409.

The following examples demonstrate various aspects of the preferred embodiments. However, a skilled artisan will readily find application for the principles described herein for preventing freezing in a number of other contexts. Examples 1 illustrates the ability of PVA to inhibit ice formation.

EXAMPLE 1

Ten 20 ml glass scintillation vials were each filled with 10 ml of purified water. 100 mg of atactic PVA (~1 kDa molecular weight, 20% vinyl acetate copolymer) was added to the water in each of five vials. The remaining five vials contained only water.

Mineral oil was added to all the vials to prevent overcooling of the meniscus edge at the water surface. The vials were suspended in air at −50° C., resulting in the water cooling at a rate of approximately 2° C. per minute. All the vials containing water without PVA froze at temperatures between −6° C. and −8° C. All the vials containing water with PVA froze at temperatures between −14° C. and −22° C. The experiment was repeated with either polyethylene glycol or polyvinyl pyrrolidone added to the water instead of PVA. These vials froze in the same temperature range as the control vials containing only water. Small quantities of PVA thus dramatically enhanced supercooling of water in 10 ml volumes.

Example 2 illustrates the utility of the invention for suppressing freezing in bulk quantities of water.

EXAMPLE 2

Two 250 ml flasks were each filled with 100 ml of purified water. 1 gram of atactic PVA (~1 kDa molecular weight, 20% vinyl acetate) was added to the water in one of the flasks. The flasks were placed in a −20° C. freezer, and the water temperature was monitored by thermocouple probes. The water in the flask without PVA was observed to freeze at −8° C. The water in the flask with PVA supercooled to −13° C. before freezing. This is an extraordinary degree of supercooling for such a large quantity of water.

Example 3 illustrates the ability of the invention to inhibit a specific ice nucleating agent (INA) of bacterial origin.

EXAMPLE 3

A solution of water was prepared containing 0.1 ppm INA extract obtained from the bacteria *Pseudomonas syringae* 31A. Several 1 microliter drops were cooled in a differential scanning calorimeter at a rate of 5° C. per minute. All the drops were observed to freeze between −7.5° C. and −9.5° C. 1% w/w atactic PVA (~1 kDa molecular weight, 20% vinyl acetate) was then added to the INA solution. Several 1 microliter drops of this solution were then cooled according to the same protocol. These drops were observed to all freeze between −9.5° C. and −12° C. The PVA clearly had an inhibitory effect on the INA, reducing the mean temperature at which ice was nucleated by approximately 2° C.

Example 4 illustrates the ability of the invention to enhance supercooling in dilute cryoprotectant solutions.

EXAMPLE 4

Two 45% w/w glycerol solutions in water were prepared. 1% w/w polyethylene glycol (~1 kDa molecular weight) was added to one solution. 1% w/w atactic PVA (~1 kDa molecular weight, 20% vinyl acetate) was added to the other solution. 10 microliter volumes of each solution were cooled in a differential scanning calorimeter at a rate of 5° C. per minute. The solution containing added polyethylene glycol froze at −39° C. The solution containing added PVA froze at −55° C. Both solutions had a nominal freezing point of approximately −20° C. Thus both solutions supercooled before freezing. However the PVA-containing solution supercooled much more deeply before freezing.

Example 5 illustrates the ability of the invention to reduce the concentration of cryoprotectants required for cryopreservation by vitrification.

EXAMPLE 5

10 ml solutions of either dimethylsulfoxide (DMSO) or glycerol cryoprotectants were prepared in water and placed in 20 ml glass scintillation vials. The vials containing DMSO were suspended in −160° C. nitrogen vapor for 16 minutes, reaching a temperature of approximately −130° C. The vials containing glycerol were suspended for 13 minutes, reaching a temperature of approximately −110° C. The vials were then inspected for signs of visible ice. The minimum cryoprotectant concentration required to prevent any visible ice from forming in the solutions (Cvit) was determined to the nearest percent. The same determination was then made as a function of added atactic PVA (~1 kDa molecular weight, 20% vinyl acetate) in the solution. The results are shown below in Table 1.

Table 1: Results of addition of PVA to the cryoprotectant concentration necessary for vitrification of DMSO and Glycerol.

| Added PVA Conc. 0% w/w | DMSO Cvit 50% w/w | Glycerol Cvit 58% w/w |
| --- | --- | --- |
| 0.001 | 49 | 57 |
| 0.01 | 48 | 55 |
| 0.1 | 48 | 54 |
| 1 | 47 | 53 |

Very small quantities of PVA were able to significantly reduce the cryoprotectant concentrations required to deep cool without ice formation (vitrify).

The following example illustrates the ability of the invention to inhibit formation of ice during rewarming of a vitrified cryoprotectant solution.

EXAMPLE 6

Two solutions of 57% w/w ethylene glycol cryoprotectant in water were prepared. Another 1% w/w ethylene glycol was added to one solution. 1% w/w atactic PVA (~1 kDa molecular weight, 20% vinyl acetate) was added to the other solution. The solutions were placed in 20 ml glass scintillation vials and cooled to −130° C. as per the protocol of Example 5. Both solutions successfully vitrified with no visible ice present at the end of cooling. The solutions were then returned to +25° C. ambient temperature air, and allowed to rewarm at a rate of approximately 8° C. per minute. At the end of six minutes of rewarming, the solution without PVA had become opaque with ice that grew during the rewarming process. In contrast, the solution with PVA was almost perfectly clear of ice, with only a few dozen very small ice growth sites visible in the solution. PVA is thus a very powerful inhibitor of ice formation during rewarming of vitrified cryoprotectant solutions.

Example 7 illustrates the ability of the invention to inhibit ice formation on the walls of containers holding vitrification solutions.

EXAMPLE 7

Two 54% w/w glycerol solutions were prepared in 20 ml glass scintillation vials. 1 ppm atactic PVA (~1 kDa molecular weight, 20% vinyl acetate) was added to one of the vials. The vials were then cooled as per the protocol of Example 5. At the end of cooling, the inside surface of the vial without PVA was covered with ice over approximately one third of the area that was in contact with the solution. In contrast, the vial containing the 1 ppm PVA additive showed no ice at all on the vial wall. There was also a tenfold decrease in the amount of ice that was visible in the solution itself. This example demonstrates the effectiveness of PVA in extremely small concentrations, and particularly the effectiveness for inhibiting nucleation of ice on surfaces.

Example 8 illustrates the ability of the invention to inhibit a bacterial INA in a vitrification solution.

EXAMPLE 8

A 56% w/w solution of ethylene glycol in water was prepared, and 0.03 ppm INA extract obtained from the bacteria *Pseudomonas syringae* 31A was added to the solution. The solution was placed in two 20 ml glass scintillation vials. An additional 1% w/w ethylene glycol was added to one vial. 1% w/w atactic PVA (~1 kDa molecular weight, 20% vinyl acetate) was added to the other vial. The two vials were then cooled as per the protocol of Example 5, and inspected for visible ice at the end of cooling. The vial without PVA contained thousands of very small ice growth sites. (If INA was not added, this 57% concentration of ethylene glycerol would ordinarily not form any ice on cooling). In contrast, the vial containing PVA showed only two ice growth sites. The PVA thus successfully inhibited this specific INA from forming ice during cooling of a vitrification solution.

The following example illustrates the ability of the invention to augment the performance of automobile antifreeze.

EXAMPLE 9

Two solutions of Prestone Low Tox (tm) propylene glycol automobile antifreeze were prepared. One solution contained 40% w/w antifreeze in tap water. The other solutions contained 39% w/w antifreeze plus 1% w/w atactic PVA (~6 kDa molecular weight, 20% vinyl acetate) in tap water. 10 ml volumes of each solution were placed in two 20 ml glass scintillation vials. A layer of mineral oil was poured on top of each solution to prevent the meniscus from cooling faster than the body of the solution. The vials were suspended in −60° C. air, resulting in a cooling rate of approximately 1° C. per minute at −30° C. The nominal freezing point of both solutions was approximately −20° C. The solution without PVA supercooled to −33° C. before freezing. The solution with PVA supercooled to −42° C. before freezing.

Example 10 illustrates the ability of the invention to successfully substitute for the activity of an antifreeze protein.

EXAMPLE 10

A 54% w/w solution of glycerol in distilled water was prepared. Three 20 ml glass scintillation vials were each filled with 10 ml of solution. 10 parts per million (ppm) of atactic PVA (~1 kDa molecular weight, 20% vinyl acetate) was added to one vial. 10 ppm of antifreeze protein from the beetle Dendroides canadensis (J Comp Physiol B 168, pp. 225–232, 1998) was added to another vial. The vials were cooled to −10° C. as per the protocol of Example 5. Upon visual examination, the vial with no additives contained several large (~2 mm) ice crystals, plus millions of tiny ice crystals giving the solution a foggy appearance. The vial with antifreeze protein contained several large ice crystals, but only a few thousand tiny ice crystals (instead of millions). The vial with PVA contained no large ice crystals, and only a few thousand tiny ice crystals similar to the vial with antifreeze protein.

What is claimed is:

1. An ice-inhibiting composition for inhibiting ice formation and ice growth comprising a compound of formula 1:

wherein R and R' are hydrogen or an alkyl group, wherein $n \geq 3$, wherein up to 25 mole percent of the hydroxyl groups are replaced with other substituents, and wherein the compound is of mean molecular weight less than 10,000 daltons and wherein the compound is present at a concentration between one part per million and 10% by weight.

2. The ice inhibiting composition of claim 1, wherein one or more of the hydroxyl groups are replaced with chemical groups selected from the group consisting of; methoxyl, alkoxyl, and amine groups.

3. The ice inhibiting composition of claim 1, wherein the compound is 1,3,5,7-heptanetetrol.

4. The ice inhibiting composition of claim 1, wherein tie compound is polyvinyl alcohol (PVA) of mean molecular weight less than 10,000 daltons.

5. The ice inhibiting composition of claim 4, wherein the PVA has a molecular weight between about 130 and 2000 daltons.

6. The ice inhibiting composition of claim 4, wherein the PVA is a copolymer consisting of 1 to 25 mole percent vinyl acetate.

7. The ice inhibiting composition of claim 6, wherein the PVA is a copolymer consisting of 10 to 20 mole percent vinyl acetate.

8. The ice inhibiting composition of claim 1, wherein the hydroxyl groups are in an atactic stereochemical arrangement.

9. The ice inhibiting composition of claim 1, wherein the hydroxyl groups are in a syndiotactic stereochemical arrangement.

10. A method of promoting the ability of water to supercool, comprising adding the ice inhibiting composition of claim 1 to the water.

11. The method of claim 10 wherein the ice inhibiting composition is added in a concentration from about one part per million to about one part in ten.

12. The method of claim 10, wherein the water is on the surface of a plant.

13. The method of claim 10, wherein the water is inside a plant.

14. The method of claim 10, wherein the water is part of an aqueous solution.

15. The method of claim 14, wherein the aqueous solution is an antifreeze solution.

16. The method of claim 15 wherein the antifreeze solution is automobile radiator coolant.

17. The method of claim 15 wherein the antifreeze solution is windshield washing fluid.

18. The method of claim 15 wherein the antifreeze solution is aircraft de-icing fluid.

19. The method of claim 15 wherein the antifreeze solution is road or runway de-icing fluid.

20. The method of claim 15, wherein the aqueous solution is a de-icing or frost prevention solution.

21. The method of claim 15, wherein the aqueous solution is a water-based paint.

22. The method of claim 15, wherein the aqueous solution occurs in wet concrete.

23. The method of claim 14, wherein the aqueous solution is a biological sample for preservation by vitrification.

24. The method of claim 23, wherein the ice inhibiting composition is present in a concentration from about 0.3% to about 3% w/w.

25. The method of claim 15 wherein the ice inhibiting composition is combined with antifreeze proteins.

26. The method of claim 14, wherein the aqueous solution is a cell or tissue preservation solution to be used to preserve biological material in a supercooled state at temperatures below 0° C.

27. A method of inhibiting the ice forming tendency of ice nucleating bacteria and the proteins produced by the bacteria, comprising adding a compound of claim 1 to surfaces or solutions containing said bacteria.

28. A method of replacing an antifreeze protein in an ice control solution comprising replacing the antifreeze protein with the composition of claim 1.

29. A method of inhibiting recrystallization of ice comprising adding the composition of claim 1 to solutions in which recrystallization is to be inhibited.

30. A method of removing ice nucleating agents from water or water solutions comprising passing the water over or through insoluble material to which is bonded the composition of claim 1.

31. A method of preventing ice nucleation in supercooled water droplets in a rain cloud comprising dispersing a composition of claim 1 from an aircraft into the atmosphere in or near said rain cloud.

32. An ice-inhibiting composition for use in hydrophobic solutions comprising a compound of formula 1:

$$[\text{—}CR_2CR'OH\text{—}]_n$$

wherein R and R' are hydrogen or an alkyl group, wherein n≧3, wherein up to 25 mole percent of the hydroxyl groups are replaced with other substituents, and wherein the compound is of mean molecular weight less than 10,000 daltons and wherein the compound is present at a concentration between one part per million and 10% by weight and wherein the compound is covalently bonded to molecules soluble in the hydrophobic solution.

33. The ice inhibiting composition of claim 32 wherein said hydrophobic solution is a fuel or oil.

34. A method of preventing freezing of water impurities in a hydrophobic fluid comprising adding the ice inhibiting composition of claim 32 to said fluid.

* * * * *